United States Patent [19]

Wolfers et al.

[11] 4,098,808
[45] Jul. 4, 1978

[54] SILYL ETHERS AND THEIR USE AS POLYMERIZATION INITIATORS

[75] Inventors: Heinrich Wolfers, Rheurdt; Hans Rudolph; Hans Jurgen Rosenkranz, both of Krefeld, all of Germany Germany

[73] Assignee: Bayer Aktiengesellschaft, Leverkusen, Germany

[21] Appl. No.: 783,935

[22] Filed: Apr. 1, 1977

[30] Foreign Application Priority Data

Apr. 7, 1976 [DE] Fed. Rep. of Germany ....... 2615039

[51] Int. Cl.$^2$ .............................................. C07F 7/18
[52] U.S. Cl. ........................................... 260/448.8 R
[58] Field of Search ................................. 260/448.8 R

[56] References Cited

U.S. PATENT DOCUMENTS

| | | |
|---|---|---|
| 2,559,342 | 7/1951 | Burkhard ...................... 260/448.8 R |
| 3,291,742 | 12/1966 | Millward ................... 260/448.8 R X |
| 3,538,137 | 11/1970 | Viventi ..................... 260/448.8 R X |

*Primary Examiner*—Paul F. Shaver
*Attorney, Agent, or Firm*—Connolly and Hutz

[57] ABSTRACT

Certain new monosilyl ethers have virtually no effect on the storage stability of unsaturated polyester resins at temperatures up to 70° C, but at higher temperatures effect rapid curing to give polymers which are substantially monomer-free.

2 Claims, No Drawings

SILYL ETHERS AND THEIR USE AS POLYMERIZATION INITIATORS

The invention relates to new silyl ethers and to a process for the initiation of polymerisation reactions which are initiated by free radical mechanisms.

It is known from German Auslegeschriften (German Published Specifications) No. 1,216,877 and 1,219,224 to use tetraaryl-glycols, in which the hydroxyl groups can be etherified, as polymerisation catalysts; furthermore, the use of tetraaryl-1,2-bis-(trialkyl- or -triarylsiloxy)-ethanes for the initiation of polymerisation reactions which proceed by a free radical mechanism is described in German Offenlegungsschriften (German Published Specifications) No. 2,131,623 and 2,164,482. These initiators are distinguished, above all, by the fact that, in contrast to the known peroxide catalysts, they can be handled completely without danger.

A further advantage is that the curing of substances which can be polymerised by a free radical mechanism and which contain these initiators can be controlled easily and reliably by a temperature programme.

However, these catalysts are not amongst those of the highest reactivity. Furthermore, larger amounts of catalyst frequently impair the properties of the cured products.

It is true that highly reactive initiators are also described in DT-OS (German Published Specification) No. 2,164,482, but substances which can be polymerised by a free radical mechanism and which contain these catalysts are not as stable on storage, at room temperature and at the temperatures of 30°–40° C which frequently arise during industrial processing, as would be desirable.

Surprisingly, it has been found that certain new monosilyl ethers have virtually no effect on the storage stability of unsaturated polyester and other resins at temperatures of up to 70° C but at higher temperatures effect, even in low concentrations, rapid through-curing to give polymer products which are substantially monomer-free.

These now monosilyl ethers, which are based on the triaryl-1,2-glycol structure, form the subject of the present invention together with a process for their preparation and their use as initiators in free radical-initiated polymerisation reactions.

The new compounds of the invention have the general formula

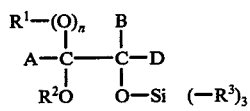
(i)

in which
A, B and D each represent an aryl radical with 6–12 C atoms optionally substituted by methyl, methoxy or chlorine;

$R^1$ represents a hydrogen atom, an alkyl radical with 1–18 C atoms, a cyloalkyl radical with 5–7 C atoms, an aralkyl radical with 6–8 C atoms or a phenyl, naphthyl or bisphenyl radical which is optionally substituted by $C_1$-$C_4$-alkyl, preferably methyl, $C_1$-$C_4$-alkoxy, preferably methoxy, or chlorine;

$R^2$ represents an alkyl radical with 1–6 C atoms, a cycloalkyl radical with 5–7 C atoms, an aralkyl radical with 6–8 C atoms or a phenyl radical which is optionally substituted by $C_1$-$C_4$-alkyl, preferably methyl, $C_1$-$C_4$-alkoxy, preferably methoxy, or chlorine;

$R^3$ represents a n-alkyl radical with 1–6 C atoms or a phenyl radical; and $n$ represents 0 or 1 (but in the case where $R_1$ represents hydrogen, $n$ represents 0).

In order to prepare these compounds, compounds of the general formula

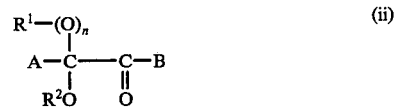
(ii)

in which
A, B, $R^1$, $R^2$ and $n$ have the abovementioned meanings, are reacted with metallo-organic compounds containing the radical D (the most suitable metallo-organic compounds for this purpose being those of general formula D-MgX or D-Li, in which D has the abovementioned meaning and X represents chlorine or bromine) and the resulting alcoholates are reacted with silicon compounds of the general formula $$Y - Si(-R^3)_3$$

in which
Y represents halogen, preferably chlorine, and
$R^3$ has the abovementioned meaning.

Silyl ethers in which $R^3$ represents methyl or phenyl are of particular importance.

Furthermore, those compounds of formula (i) in which A, B and D denote identical or different optionally substituted phenyl radicals are preferred polymerisation reaction initiators.

The compounds in the following table may be mentioned as examples of free radical initiators which are particularly suitable:

| No. | $R^1$ | $R^2$ | $R^3$ | A | B | C | n |
|---|---|---|---|---|---|---|---|
| I | —H | $H_3C$—CH—$CH_3$ | —$CH_3$ | —$C_6H_5$* | —$C_6H_5$ | —$C_6H_5$ | 0 |
| II | —$CH_3$ | $H_3C$—CH—$CH_3$ | —$CH_3$ | —$C_6H_5$ | —$C_6H_5$ | —$C_6H_5$ | 0 |
| III | —H | $H_3C$—$H_2C$—CH—$CH_3$ | —$CH_3$ | —$C_6H_5$ | —$C_6H_5$ | —$C_6H_5$ | 0 |

-continued

| No. | R¹ | R² | R³ | A | B | C | n |
|---|---|---|---|---|---|---|---|
| IV | H₃C—CH—CH₃ | —CH₃ | —CH₃ | —C₆H₅ | —C₆H₅ | p-CH₃—C₆H₄—C₆H₅ | 0 |
| V | —H | —C₆H₅ | —CH₃ | —C₆H₅ | —C₆H₅ | —C₆H₅ | 0 |
| VI | —CH₃ | —C₂H₅ | —CH₃ | —C₆H₅ | —C₆H₅ | o-Cl—C₆H₄—C₆H₅ | 0 |
| VII | H₂C—C₆H₄ | H₃C—CH—CH₃ | —CH₃ | —C₆H₅ | —C₆H₅ | —C₆H₅ | 0 |
| VIII | n-C₁₂—H₂₅ | H₃C—CH—CH₃ | —CH₃ | —C₆H₅ | p-CH₃—C₆H₄ C₆H₅ | p-CH₃—C₆H₄—C₆H₅ | 0 |
| IX | —H₂C—(Cl-phenyl) | —CH₃ | —CH₃ | —C₆H₅ | —C₆H₅ | —C₆H₅ | 0 |
| X | —CH₃ | —CH₃ | —CH₃ | —C₆H₅ | —C₆H₅ | p-CH₃—C₆H₄—C₆H₅ | 1 |
| XI | —C₂H₅ | —C₂H₅ | —CH₃ | —C₆H₅ | —C₆H₅ | —C₆H₅ | 1 |
| XII | —H | H₃C—H₂C—CH—CH₃ | —C₆H₅ | —C₆H₅ | —C₆H₅ | —C₆H₅ | 0 |

* —C₆H₅ represents —(phenyl ring)

The compounds listed under Numbers I, II, III and XI in the table are free radical initiators which are particularly suitable.

The silyl compounds according to the invention are suitably added to the substance to be polymerised, or to the mixture of substances to be polymerised, in amounts of 0.02–1, and preferably 0.05–0.5 % by weight, relative to the substance or mixture to be polymerised and, at temperatures of up to 70° C, they display, in this substance or mixture, no polymerisation-initiating activity even after storing for several days. The formation of free radicals starts only when the initiators according to the invention, in the substance or mixture of substances to be polymerised are heated to a temperature of, preferably, above 100° C up to about 250° C.

The polymerisation will usually take place in a single stage but can optionally be carried out stepwise by means of a suitable temperature programme. (Compare British Patent Specification No. 1,041,614).

Substances which can be polymerised using the free redical initiators of the invention include virtually all compounds which contain, per molecule, one or more double bonds which are capable of polymerisation. Examples are aromatic vinyl compounds (such as styrene and vinyltoluene), α,β-olefinically unsaturated carboxylic acids and their derivatives (such as (meth)acrylonitrile and (meth)acrylates, vinyl halides e.g. vinyl chloride, vinylidene, halides e.g. vinylidene, chloride, conjugated diolefines (such as butadiene, isoprene and chloroprene), as well as divinylbenzene, di-(vinylphenyl) carbonates, diallyl phthalate, diallyl carbonate, di-(allylphenyl) carbonates, polyolpoly-(meth)-acrylates, N,N'-methylene-bis-(meth)acrylamide and diallyl fumarate.

The polymerisation initiators according to the invention are particularly suitable for use in the polymerisation of moulding compositions and coating compositions which contain unsaturated polyester resins and vinyl or vinylidene compounds which can be copolymerised therewith.

In the sence of the invention, α,β-ethylenically unsaturated polyesters are the customary polycondensation products of at least one α,β-ethylenically unsaturated dicarboxylic acid with, as a rule, 4 or 5 C atoms, or ester-forming derivatives thereof, optionally mixed with up to 90 mol %, relative to the unsaturated acid component, of at least one aliphatic saturated dicarboxylic acid with 4–10 C atoms, or a cycloaliphatic dicarboxylic acid with 8–10 C atoms, or ester-forming derivatives thereof, with at least one polyhydroxy compound, especially a dihydroxy compound, with 2–8 C atoms; that is to say polyesters such as are described in J. Björksten et al., "Polyesters and their Applications", Reinhold Publishing Corp., New York 1956.

Examples of unsaturated dicarboxylic acids, or their derivatives, which are preferably used in the manufacture of polyesters are maleic acid (or maleic anhydride) and fumaric acid. However, it is also possible, for example, to use mesaconic acid, citraconic acid, itaconic acid or chloromaleic acid. Examples of aliphatic saturated dicarboxylic acids and cycloaliphatic dicarboxylic acids, or their derivatives, which may be used are phthalic acid (or phthalic anhydride), isophthalic acid, terephthalic acid, hexahydrophthalic acid or tetrahydrophthalic acid (or their anhydrides), endomethylenetetrahydrophthalic acid (or its anhydride), succinic acid (or succinic anhydride) and succinic acid esters and succinic acid chlorides, adipic acid and sebacic acid. In order to prepare resins of low inflammability it is possible, for example, to use hexachloroendomethylenetetrahydrophthalic acid (Het-acid), tetrachlorophthalic acid or tetrabromophthalic acid. Preferred polyesters are those which contain maleic acid radicals, up to 25 mol % of which can be replaced by phthalic acid radicals or isophthalic acid radicals. Dihydric alcohols which can be employed are ethylene glycol, propane-1,2-diol, propane-1,3-diol, diethylene glycol, dipropylene glycol, butane-1,3-diol, butane-1,4-diol, neopentylglycol, hexane-1,6-diol, 2,2-bis-(4-hydroxycyclohexyl)-propane, bis-oxalkylated bisphenol A and perhydrobisphenol. Ethylene glycol, propane-1,2-diol, diethylene glycol and dipropylene glycol and preferably used.

Further modification to the polyester are possible by incorporating up to 10 mol %, relative to the alcohol or acid component, of monohydric, trihydric and tetrahydric alcohols with 1–6 C atoms, such as methanol, ethanol, butanol, allyl alcohol, benzyl alcohol, cyclohexanol and tetrahydrofurfuryl alcohol, trimethylpropane, glycerol and pentaerythritol, as well as of mono-, di- and tri-allyl ethers and benzyl ethers of trihydric and more highly hydric alcohols with 3–6 C atoms according to DAS (German Published Specification) No. 1,024,654, and also by incorporating monobasic acids, such as benzoic acid, or longchain unsaturated fatty acids, such as oleic acid, linseed oil fatty acid and dehydrated ricinoleic acid.

The acid numbers of the polyesters should be between 1 and 100 and preferably between 20 and 70, the OH numbers should be between 10 and 150, preferably between 20 and 100, and the molecular weights $\overline{M}_n$, should be between about 500 and 5,000 and preferably between about 1,000 and 3,000 (determined by vapour pressure osmometry in dioxane and acetone; in the case of differing values, the lower value is taken as being correct).

Copolymerisable vinyl and vinylidene compounds which are suitable in the sense of the invention are unsaturated compounds which are customarily used in polyester technology and which preferably carry α-substituted vinyl groups or β-substituted allyl groups, preferably styrene, but also, for example, styrenes which are chlorinated and alkylated or alkenylated in the nucleus, it being possible for the alkyl groups to contain 1–4 carbon atoms, such as, for example, vinyltoluene, divinylbenzene, α-methylstyrene, tert.-butylstyrene and chlorostyrenes; vinyl esters of carboxylic acids with 2–6 carbon atoms, preferably vinyl acetate; vinylpyridine, vinylnaphthalene, vinylcyclohexane, acrylic acid and methacrylic acid and/or their esters (preferably the vinyl, allyl and methallyl esters) with 1–4 carbon atoms in the alcohol component, and their amides and nitriles, maleic anhydride and maleic acid semi-esters and diesters with 1–4 carbon atoms in the alcohol component, maleic acid semi-amides and di-amides or cyclic imides, such as N-methylmaleimide or N-cyclohexylmaleimide; and allyl compounds, such as allylbenzene and allyl esters, such as allyl acetate, phthalic acid diallyl ester, isophthalic acid diallyl ester, fumaric acid diallyl ester, allyl carbonates, diallyl carbonates, triallyl phosphate and triallyl cyanurate.

By means of a simple colour reaction it is possible to test the temperature of the dissociation of the particular catalyst as this becomes noticeable, and thus to test the optimum range for use of the catalyst. This test is possible because free radicals which are formed during the thermal decomposition are able to decolorise quinonoid dyestuffs, so that it is possible to detect the start of the formation of free radicals. In order to carry out this test, the quinonoid dyestuff is dissolved in a solvent which is free from oxygen, such as glycol or xylene, and a small amount of the compound is added. The temperature at which discoloration takes place is the temperature above which a dissociation reaction which becomes significant starts.

The following Examples are given for the purpose of illustrating the invention.

EXAMPLE 1

Preparation of
1-isopropoxy-1-phenyl-2-trimethylsiloxy-2,2-diphenylethane I 2.3 g of dry magnesium filings are initially introduced into 100 cc of absolute tetrahydrofuran in a three-necked flask fitted with a stirrer, a reflux condenser, a dropping funnel and a gas inlet tube. Whilst flushing with nitrogen, 5 g of bromobenzene are added at room temperature. After the reaction has started, further bromobenzene (10.5–11 g) is metered in until all of the magnesium has dissolved. A solution of 25.6 g of benzoin isopropyl ether in 120 cc of absolute tetrahydrofuran is then added dropwise at 0°–10° C. After the addition, the mixture is stirred for 3 hours at room temperature, 12.5 g of trimethylchlorosilane are then added and the mixture is stirred, first for a further 4 hours at room temperature and then for a further 2 hours at 50° C.

After cooling, the batch is poured onto ice, the organic phase is separated off and washed twice with water and the aqueous phase is extracted once with diethyl ether. The combined organic phases are dried and then freed from solvent. The residue is recrystallised from ethanol.

Yield: 36 g
Melting point: 39° C
$H_1$-NMR (in $CDCl_3/CH_2Cl_2$; δ[ppm]): 5.45 s, 3.72 m, 1.40 d, 1.18 d, aromatic protons 7–7.5 – 0.02 S

EXAMPLE 2

1-Isopropoxy-1-methyl-1-phenyl-2-trimethylsiloxy-2,2-diphenylethane II

Example 1 is repeated with the exception that 26.8 g of -methylbenzoin isopropyl ether are employed in place of the benzoin isopropyl ether.

Yield: 36 g = 87% of theory
Melting point: 80° C.
$H_1$-NMR (in $CDCl_3/CH_2Cl_2$; δ[ppm]): 3.80 m, 1.86 s, 1.46 d, 1,25 d and -0.02 s; aromatic protons 7.0–7.7

EXAMPLE 3

Preparation of
1-isobutoxy-1-phenyl-2-trimethylsiloxy-2,2-diphenylethane III

Example 1 is repeated with the exception that 26.8 g of benzoin sec.-butyl ether are employed in place of the benzoin isopropyl ether.

Residue: 37 g = 89% of a yellow oil.
$H_1$-NMR (in $CDCl_3/CH_2Cl_2$; δ/ppm/: 5.42 s, 3.68 m, 1.75 m, 0.9–1.2 m and 0.08 s; aromatic protons 7–7.5.

EXAMPLE 4

Preparation of
1,1-diethoxy-1-phenyl-2-trimethylsiloxy-2,2-diphenylethane XI

Example 1 is repeated with the exception that 28.4 g of benzil diethyl ketal are employed in place of the benzoin isopropyl ether. After evaporating in a rotary evaporator, 34 g (78%) of a yellow oil remain.
$H_1$-NMR (in $CDCl_3/CH_2Cl_2$; δ[ppm]): 3.75 q, 1.25 t and -0.02 s; aromatic protons 7.0–7.9.

In the examples which follow the parts indicated denote - unless otherwise stated - parts by weight.

EXAMPLE 5

An unsaturated polyester resin prepared from 11 parts of o-phthalic anhydride, 47 parts of maleic anhydride and 42 parts of propylene 1,2-glycol at 200° C, is dissolved in styrene to give a 66% solution and the solution is stabilised with 0.01 part of hydroquinone.

0.1 part of an initiator of the formula II

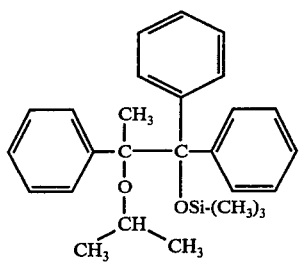

(II)

is dissolved in this solution. 20 g of this resin mixture are filled into a test tube with an internal diameter of 16 mm. An iron/constantan thermo-element, which is connected to a temperature/time recorder, is dipped 3 cm deep into the resin. One hour after the catalyst has been mixed in, the test tube, which is filled to a height of 8 cm, is dipped into a thermostat-controlled oilbath at the same time as the measuring apparatus is switched on. The curing times (time taken to reach the peak temperature minus the time which elapses before the 65° C line is crossed) and the peak temperatures are determined analogously to DIN 16,945.

At the indicated bath temperatures, the following values are obtained:

| Bath temperature [° C] | Curing time [minutes] | Peak temperature [° C] |
|---|---|---|
| 120 | 6.5 | 255 |
| 130 | 4.7 | >260 |
| 140 | 3.2 | >260 |
| 150 | 2.1 | >260 |

EXAMPLE 6

Example 5 is repeated with the exception that the resin, after mixing with the catalyst, is subjected to heat treatment at 70° C for 5 days prior to curing. The viscosity of the resin does not change as a result of this treatment and the curing experiments at 120°–140° C give the same curing times and peak temperatures.

EXAMPLE 7

(Comparison experiment)

Example 5 is repeated; however, 0.75 part of di-tert.-butyl peroxide is stirred in instead of the initiator of formula II. At a bath temperature of 140° C, the curing time is 2.2 minutes. A maximum temperature of 235° C is reached. When the polyester which has been mixed with the peroxide but has not been cured is stored at 70° C, the resin gels after 20 hours.

EXAMPLE 8

Example 5 is repeated but the amount of catalyst of formula II is increased to 0.3 part. At this concentration, the following values are obtained for the measured bath temperatures:

| Bath temperature [° C] | Curing time [minutes] | Peak temperature [° C] |
|---|---|---|
| 120 | 4.4 | >260 |
| 130 | 3.3 | >260 |
| 140 | 2.4 | >260 |
| 150 | 1.9 | >260 |

EXAMPLE 9

Example 8 is repeated with the exception that the resin, after mixing with the catalyst, is subjected to heat treatment at 70° C for 5 days prior to curing. The viscosity of the resin does not change as a result of this treatment and the curing experiments at a bath temperature of 120°–150° C give the same curing times and peak temperatures.

EXAMPLE 10

100 parts of a polyester resin according to Example 5 are dissolved in styrene to give a 66% solution, the solution is stabilised with 0.01 part of hydroquinone and 100 parts of chalk, 4 parts of zinc stearate and 3.75 parts of magnesium oxide paste are mixed in. After 0.3 part of the initiator of the formula II has been added, the resin cures thoroughly in the course of 3 minutes under the conditions described in Example 5, at a bath temperature of 140° C. A maximum temperature of 210° C is reached.

EXAMPLE 11

An unsaturated polyester resin, prepared from 84 parts of o-phthalic anhydride, 98 parts of maleic anhydride and 114 parts of propylene 1,2-glycol at 200° C, is dissolved in styrene to give a 66% solution and the solution is stabilised with 0.01 part of hydroquinone. Equal portions of this resin are mixed with 0.1% and with 0.3% respectively of an initiator of formula II and cured as described in Example 5.

| Initiator concentration % | Bath temperature [° C] | Curing time [minutes] | Peak temp. [° C] |
|---|---|---|---|
| 0.1 | 130 | 4.6 | 240 |
| 0.1 | 140 | 3.2 | 250 |
| 0.1 | 150 | 2.7 | >260 |
| 0.3 | 130 | 3.4 | 250 |
| 0.3 | 140 | 2.6 | >260 |
| 0.3 | 150 | 2.2 | >260 |

EXAMPLE 12

Example 11 is repeated with the exception that the resin, after mixing with the catalyst of formula II, is subjected to heat treatment at 70° C for 5 days prior to curing. The viscosity of the resin does not change and the polymerisation experiments at 120°–140° C give the same curing times and peak temperatures.

EXAMPLE 13

0.8 g of each of the two initiators numbered I and II in the table above is added to, in each case, 400 g of styrene. The solutions are each divided into four 100 g portions and subjected, together with four comparison samples of technical grade styrene, to heat treatment at 110° C. A sample is taken from each series after certain times and the amount of polymerised styrene is determined by precipitation with, in each case, 500 g of methanol.

| Polymerisable substance | Polymerisation time [hrs] | | | |
|---|---|---|---|---|
| | 1 | 2 | 3 | 4 |
| Technical grade styrene | — | 0.7 | 7.5 | 16 |
| Technical grade styrene + 0.2% of initiator I | — | 1.2 | 15.5 | 30.5 |
| Technical grade styrene + |  |  |  |  |

-continued

| Polymerisable substance | Polymerisation time [hrs] | | | |
|---|---|---|---|---|
| | 1 | 2 | 3 | 4 |
| 0.2% of initiator II | 1.9 | 13.2 | 28.3 | 40.4 |

EXAMPLE 14

0.1 part of each of the initiators numbered II and XI above is added to 33.3% strength solutions of butyl acrylate in toluene and the solutions, in several portions of 30 g each, are heated to the boil. Samples are taken after certain times, 1 ml of a 4% strength solution of hydroquinone in ethyl acetate is added to each sample and the samples are then poured into an open dish. The solvents are evaporated by heating to 100° C for 16 hours and the residual monomers are removed by subjecting the residue to heat treatment at 160° in a vacuum drying cabinet (200 mm Hg).

Gravimetric determination of the residues gives the following proportions of polymerised substance [% of the sample weight]:

| Initiator | Polymerisation time [minutes] | | | |
|---|---|---|---|---|
| | 15 | 30 | 60 | 120 |
| II | 21 | 44 | 75 | 97 |
| XI | 17 | 35 | 50 | 92 |
| none | 1 | 3 | 5 | 7 |

We claim:
1. Silyl ethers of the formula

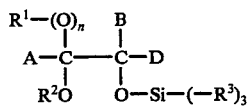  (I)

in which

A, B and D represent aryl radicals with 6–12 C atoms which are optionally substituted by methyl, methoxy or chlorine, $R^1$ represents hydrogen, an alkyl radical with 1–18 C atoms, a cycloalkyl radical with 5–7 C atoms, an aralkyl radical with 6–8 C atoms or a phenyl, naphthyl or biphenyl radical which is optionally substituted by $C_1$-$C_4$-alkyl, $C_1$-$C_4$-alkoxy, or chlorine, $R^2$ represents alkyl radicals with 1–6 C atoms, cycloalkyl radicals with 5–7 C atoms, aralkyl radicals with 6–8 C atoms and a phenyl radical which is optionally substituted by $C_1$-$C_4$-alkyl, $C_1$-$C_4$-alkoxy, or chlorine, $R^3$ represents a n-alkyl radical with 1–6 C atoms or a phenyl radical and $n$ represents 0 or 1 (but in the case where $R_1$ denotes hydrogen, represents only 0).

2. Process for the preparation of silyl ethers according to claim 1, characterised in that compounds of the formula

  (II)

in which

A, B, $R^1$, $R^2$ and $n$ have the abovementioned meaning, are reacted with metallo-organic compounds, preferably D-Mg-X or D-Li, in which D has the abovementioned meaning and X represents chlorine or bromine, and the ethers are formed from the resulting alcoholates using silicon compounds of the formula

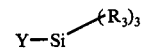

in which

Y is halogen, preferably chlorine, and $R_3$ has the abovementioned meaning.

* * * * *